United States Patent
Baumgarten et al.

(10) Patent No.: US 7,294,744 B2
(45) Date of Patent: Nov. 13, 2007

(54) PROCESS FOR MANUFACTURING OF ENANTIOMERICALLY PURE 3-HYDROXY-3-PHENYL-PROPYLAMIN

(75) Inventors: Wolfgang Baumgarten, Gau-Algesheim (DE); Robert Schiffers, Gau-Algesheim (DE)

(73) Assignee: Boehringer Ingelheim Pharma GmbH & Co. KG (DE)

( * ) Notice: Subject to any disclaimer, the term of this patent is extended or adjusted under 35 U.S.C. 154(b) by 244 days.

(21) Appl. No.: 11/174,086

(22) Filed: Jun. 30, 2005

(65) Prior Publication Data

US 2006/0009533 A1    Jan. 12, 2006

(30) Foreign Application Priority Data

Jul. 8, 2004   (DE) ............... 10 2004 033 313

(51) Int. Cl.
*C07C 209/78* (2006.01)
(52) U.S. Cl. .................................... 564/358
(58) Field of Classification Search ............. 564/358
See application file for complete search history.

(56) References Cited

U.S. PATENT DOCUMENTS

| | | | | |
|---|---|---|---|---|
| 4,879,389 A | * | 11/1989 | Achiwa | 548/412 |
| 4,985,567 A | * | 1/1991 | Achiwa et al. | 548/412 |
| 6,187,956 B1 | * | 2/2001 | Klinger et al. | 564/358 |
| 6,218,575 B1 | * | 4/2001 | Klingler et al. | 564/358 |
| 7,049,469 B2 | * | 5/2006 | Kreye et al. | 564/304 |

OTHER PUBLICATIONS

Takahashi et al., J. Am. Chem. Soc. (1990), 112(15), p. 5876-5878.*
Database CAPLUS on STN, Acc. No. 1992:20725, Sakuraba et al., Synlett (1991), 10, p. 689-690 (abstract).*
Database CAPLUS on STN, Acc. No. 1993:559860, Achinami et al., JP 05070412 (Mar. 23, 1993) (abstract).*
Database CAPLUS on STN, Acc. No. 1995:741631, Sakuraba et al., Chemical & Pharmaceutical Bulletin (1995), 43(5), p. 748-753 (abstract).*

* cited by examiner

*Primary Examiner*—Brian Davis
(74) *Attorney, Agent, or Firm*—Michael P. Morris; Mary-Ellen M. Devlin

(57) ABSTRACT

The present invention relates to an improved process for preparing enantiomerically pure 3-hydroxy-3-phenyl-propylamines on an industrial scale using asymmetrical hydrogenation as a key step and optionally a special sequence of subsequent steps, using a catalyst system consisting of rhodium and chiral 4-(dicyclohexylphosphino)-2-(diphenyl-phosphino-methyl)-N-methyl-aminocarbonyl-pyrrolidine.

17 Claims, No Drawings

PROCESS FOR MANUFACTURING OF ENANTIOMERICALLY PURE 3-HYDROXY-3-PHENYL-PROPYLAMIN

The present invention relates to an improved process for preparing enantiomerically pure 3-hydroxy-3-phenyl-propylamines by rhodium-catalysed asymmetric hydrogenation on an industrial scale.

BACKGROUND TO THE INVENTION

The pure enantiomers of the 3-hydroxy-3-phenyl-propylamine of formula I

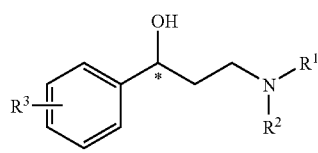

I are valuable intermediate products for the synthesis of pharmaceutical active substances such as e.g. R-atomoxetine, S-fluoxetine or S-norfluoxetine, which belong to the norepinephrine and serotonin reuptake inhibitors used pharmaceutically as antidepressants or agents for treating urinary incontinence and are of great commercial interest. The chemical structure of the three compounds mentioned by way of example are shown in formulae A-C:

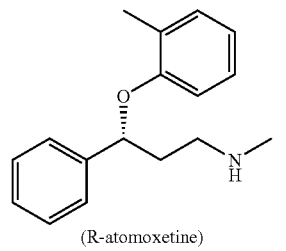

A (R-atomoxetine)

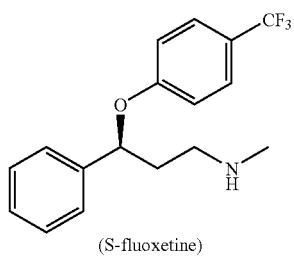

B (S-fluoxetine)

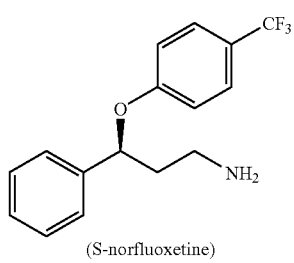

C (S-norfluoxetine)

PRIOR ART

Numerous alternative methods of producing enantiomerically pure phenylpropylamines are disclosed in the prior art Sharpless et al. propose enantioselective epoxidation (J. Org. Chem. 1988, 53, 4081) for preparing enantiomerically pure compounds of this type.

Corey et al. propose enantioselective oxyborolidine-catalysed ketone reduction (Tetrahedron Lett. 1989, 30 5207) for preparing enantiomerically pure compounds of this type.

Koenig et al. indicate a conventional chemical method for preparing a racemic phenylpropylamine with subsequent racemate cleavage using chiral mandelic acid (Tetrahedron Lett. 1994, 35, 1339).

T. Ohkuma et al. propose in Organic Letters 2000, Vol. 2 No. 12 1749-1751 the enantioselective hydrogenation of 3-dimethylamino-1-(2-thienyl)-propanone using a chiral ruthenium catalyst in the presence of potassium tert-butoxide.

However, the methods described in the prior art are not really suitable for preparing N-benzyl-N-methyl-3-hydroxy-3-(2-thienyl)-propylamines on an industrial scale, as either the optical purity achieved is inadequate or large amounts of chiral reduction systems have to be used for the enantioselective reduction which are difficult to obtain and in some cases unstable.

One of the main objectives of the present invention is to provide a method by which 3-hydroxy-3-phenyl-propylamines I can be prepared with high optical and chemical purity, preferably on an industrial scale. At the same time the risk of, for example, contaminating a pharmaceutical composition with the unwanted enantiomers is to be minimised.

Another aim of the invention is to provide a method by which substantially enantiomerically pure 3-hydroxy-3-phenyl-propylamines can easily be prepared from readily available starting materials.

An additional aim of the invention is to provide a process by which R-atomoxetine, S-fluoxetine and S-norfluoxetine may be prepared in a high optical and chemical purity.

Surprisingly it has now been found that 3-hydroxy-3-phenyl-propylamines I can be obtained in the form of the R or S-enantiomer on an industrial scale in good yields and with very good optical purity if a corresponding 1-amino-3-(phenyl)-propan-3-one II

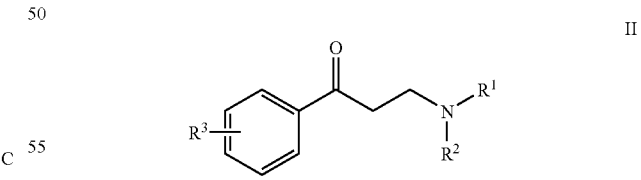

II is reacted in an asymmetrical hydrogenation in the presence of rhodium and a chiral, bidentate phosphine ligand as catalyst system.

DESCRIPTION OF THE INVENTION

The present invention relates to a process for preparing chiral, optically pure 3-hydroxy-3-phenyl-propylamines of formula I,

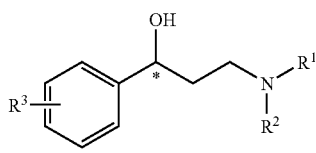

wherein
R¹ denotes H, —C₁₋₆-alkyl or —C₇₋₁₈-aralkyl, preferably H, methyl, ethyl, iso-propyl, tert-butyl or benzyl, particularly preferably H, methyl, or benzyl;

R² denotes H, —C₁₋₆-alkyl or —C₇₋₁₈-aralkyl, preferably H, methyl, ethyl, iso-propyl, tert-butyl or benzyl, particularly preferably H, methyl or benzyl;

R³ denotes
  H, —C₁₋₆-alkyl, —OH, —O—C₁₋₆-alkyl, —O—C₇₋₁₈-aralkyl, —OOC—C₁₋₆-alkyl, —OOC-aryl, halogen, preferably H, methyl, iso-propyl, tert-butyl, hydroxy, methoxy, propoxy, butoxy, benzyloxy, acetyloxy, benzoyloxy, F, Cl or Br; particularly preferably H, hydroxy, methoxy, benzyloxy, acetyloxy or benzoyloxy;

or an acid addition salt thereof, starting from 1-amino-3-(phenyl)-propan-3-one of formula II,

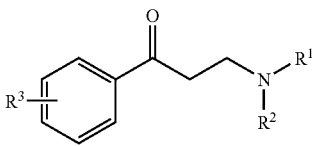

wherein R¹, R², and R³ are as hereinbefore defined, or an acid addition salt thereof, characterised in that it is subjected to asymmetrical hydrogenation in the presence of a catalyst system consisting of rhodium and chiral 4-(dicyclohexylphosphino)-2-(diphenylphosphino-methyl)-N-methyl-aminocarbonyl-pyrrolidine, optionally an inert diluent and a weak base.

The compound II to be used as starting product is obtained by reacting the 1-phenylethanone substituted by R³ with a correspondingly substituted amine and formaldehyde in a Mannich reaction. Preferably the enantioselective hydrogenation is carried out in the absence of a diamine.

Preferably the process described above is for preparing chiral 3-hydroxy-3-phenyl-propylamines of formula I, wherein
R¹ denotes H, methyl, ethyl, iso-propyl, tert-butyl or benzyl;
R² denotes H, methyl, ethyl, iso-propyl, tert-butyl or benzyl;
R³ denotes H, methyl, iso-propyl, tert-butyl, hydroxy, methoxy, propoxy, butoxy, benzyloxy, acetyloxy, benzoyloxy, F, Cl or Br;

Preferably the process described above is for preparing chiral 3-hydroxy-3-phenyl-propylamines of formula I, wherein
R¹ denotes H, methyl or benzyl;
R² denotes H, methyl or benzyl;
R³ denotes H, hydroxy, methoxy, benzyloxy, acetyloxy or benzoyloxy.

Preferably the process described above is for preparing chiral 3-hydroxy-3-phenyl-propylamines of formula I, wherein
R¹ denotes H, methyl or benzyl;
R² denotes H, methyl or benzyl;
R³ denotes H.

A catalyst system consisting of rhodium and (2R, 4R)-4-(dicyclohexylphosphino)-2-(diphenylphosphino-methyl)-N-methyl-aminocarbonyl-pyrrolidine (RR-MCCPM) yields the corresponding S-3-hydroxy-3-phenyl-propylamine I-S as product.

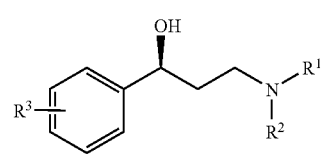

The above process is therefore preferably used to prepare S-3-hydroxy-3-phenyl-propylamines I-S, wherein the catalyst system consists of rhodium and (2R,4R)-4-(dicyclohexylphosphino)-2-(diphenylphosphino-methyl)-N-methyl-aminocarbonyl-pyrrolidine.

A catalyst system consisting of rhodium and (2S,4S)-4-(dicyclohexylphosphino)-2-(diphenylphosphino-methyl)-N-methyl-aminocarbonyl-pyrrolidine (SS-MCCPM) yields the corresponding R-3-hydroxy-3-phenyl-propylamine I-R as product.

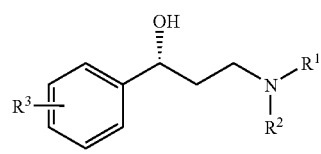

The above process is therefore preferably used to prepare R-3-hydroxy-3-phenyl-propylamines I-R, wherein the catalyst system consists of rhodium and (2S,4S)-4-(dicyclohexylphosphino)-2-(diphenylphosphino-methyl)-N-methyl-aminocarbonyl-pyrrolidine.

The reaction is preferably carried out in the presence of a weak base. The base used may be an organic base or inorganic base, both in solid form and in the form of solutions, e.g. aqueous solutions. Suitable inorganic bases are basically reacting alkali metal salts or alkali metal hydroxides. Preferably, alkali metal hydrogen carbonates or alkali metal carbonates are used in addition to alkali metal hydroxides. Most particularly preferred are Na₂CO₃, K₂CO₃, LiOH, NaOH, KOH or NaHCO₃.

Suitable organic bases are tertiary amines, particularly tertiary alkylamines, tertiary alkyl-arylamines or pyridine or the free base of formula II which is present in excess. Preferably, trialkylamines with branched or unbranched —C₁₋₆-alkyl groups are used. Triethylamine or diisopropylethylamine, for example, have proved most particularly preferable. If desired, the reaction may also be carried out in the presence of basic polymers with e.g. tertiary amino functions.

A process is preferred wherein the asymmetric hydrogenation is carried out in a temperature range of from 0° C. to 100° C., preferably 0° C. to 50° C., particularly 20° C. to 40° C.

Also preferred is a process wherein the asymmetric hydrogenation is carried out under a pressure of 1-150 bar, preferably under a pressure of 50-150 bar, particularly at about 80-120 bar, particularly preferably 100 bar.

The inert diluents used may be both protic solvents—such as e.g. alcohols and/or water—or aprotic polar solvents such as e.g. ethers and/or amides or lactams and/or mixtures thereof. Water may optionally be added to all the solvents. The protic solvents used are preferably branched or unbranched $C_{1-8}$-alcohols. Particularly preferred are lower alcohols such as methanol, ethanol, n-propanol and iso-propanol or mixtures thereof. Methanol is particularly preferred as the reaction medium, while the methanol or other alcohols or solvents may optionally contain water. Suitable aprotic solvents are polar ethers such as for example tetrahydrofuran or dimethoxyethylether or amides such as for example dimethylformamide, or lactams such as for example N-methylpyrrolidone. It is preferable to use solvents which have low tendency to flammability.

Preferably, processes are used in which II or the acid addition salts thereof are used in a molar ratio to the rhodium catalyst of 500:1 to 100000:1, preferably from 750:1 to 20000:1, during the asymmetrical hydrogenation.

At a molar ratio of catalyst to substrate of about 1:2000 (S)-N-alkyl-N-methyl-3-hydroxy-3-(2-thienyl)-propylamine is obtained from 1-(N-alkyl-N-methylamino)-3-(2-thienyl)-propan-3-one hydrochloride by the process according to the invention in an optical purity of >94% ee.

The preparation of this catalyst is known from the prior art [EP 0 251 164 and EP 0 336 123]. The catalyst may also be present in polymer-bound form, e.g. with the chiral ligand 4-dicyclohexylphosphino)-2-(diphenylphosphino-methyl)-N-methyl-aminocarbonyl)pyrrolidine bound to a polymer e.g. via the phenyl groups. The use of polymer-bound ligands of this kind does not necessarily rule out the use of non-polymer-bound ligands at the same time. Polymer-bound catalysts of this kind are particularly advantageous for easy purification of the product.

The catalyst is used either as a pre-prepared, oxygen-free solution of $[Rh(COD)Cl_2]_2$ and ligand or prepared in situ from $[Rh(COD)Cl_2]_2$ and ligand in the presence of 1-amino-3-phenyl-propan-3-one under oxygen-free conditions under a protective gas atmosphere or hydrogen atmosphere.

In order to prepare an S-enantiomer of formula I-S the catalyst used according to the invention is $[Rh(COD)Cl_2]_2$, wherein COD denotes a cyclooctadienyl group, and (2R, 4R)-4-(dicyclohexylphosphino)-2-(diphenylphosphino-methyl)-N-methyl-aminocarbonylpyrrolidine (RR-MCCPM) as a chiral, bidentate phosphine ligand (PP*).

In order to prepare an R-enantiomer of formula I-R the catalyst used according to the invention is $[Rh(COD)Cl_2]_2$, wherein COD denotes a cyclooctadienyl group, and (2S, 4S)-4-(dicyclohexylphosphino)-2-(diphenylphosphino-methyl)-N-methyl-aminocarbonylpyrrolidine (SS-MCCPM) is used as a chiral bidentate phosphine ligand (PP*).

The hydrogenation is generally carried out in oxygen-free conditions, conveniently under inert gas, preferably under a hydrogen atmosphere. However, it is not essential for the reaction that the hydrogen for the hydrogenation can be derived from the atmospheric gas through the reaction mixture. The hydrogen may also be produced in situ in solution from suitable hydrogen sources. Hydrogen sources of this kind include e.g. ammonium formate, formic acid and other formates, hydrazines in the presence of metal ions such as $Fe^{2+}/Fe^{3+}$ and other hydrogen sources known from the prior art.

The reaction time for the asymmetric hydrogenation is generally between 2 and 48 hours up to its end, preferably between 4 and 36 hours, particularly preferably about 18 to 22 hours.

The reaction may be worked up ion the conventional manner, e.g. by optionally deactivating the catalyst and removing it, eliminating the solvent from the residue and isolating the pure end product by crystallisation, distillation, extraction or chromatography.

Preferably, the following steps are carried out in order to work up and isolate the product:
(i) dividing the reaction mixture obtained in the asymmetrical hydrogenation between water and an organic solvent,
(ii) adjusting a pH value of the aqueous phase in the acid range,
(iii) separating off the aqueous phase,
(iv) optionally repeating steps (i) to (iii)
(v) adjusting the pH value of the aqueous phase in the basic range;
(vi) dividing the reaction mixture between water and an organic solvent,
(vii) optionally repeating steps (v) to (vi)
(vii) separating off the organic phase formed and concentrating it.

The adjustment of the pH value of the aqueous phase in the acidic range in step (ii) serves to form the salt of the hydrogenated product, so as to increase the solubility of the product in the aqueous phase. The pH selected for this purpose depends on the product, and is preferably from 1-2, particularly preferably from 1.2-1.8. The adjustment of the pH of the aqueous phase in the basic range in step (v) serves to bring the hydrogenated product out of its salt form, so as to increase the solubility of the product in the organic phase. The pH selected for this purpose again depends on the product and is preferably 6-10, particularly preferably 7-9.

Particularly for working up and isolating the product after enantioselective hydrogenation the reaction mixture obtained is evaporated down and the solid obtained is divided between water and an organic solvent, preferably toluene or dichloromethane. The pH of the aqueous phase is adjusted to a value of 1 to 2, preferably 1.2 to 1.8, and then the aqueous phase is separated off. The organic phase is preferably again combined with water, acidified and separated off again. The combined aqueous phases are adjusted to a pH of 8 to 10, preferably 8.5 to 9.5, combined with solvent and extracted. The corresponding 3-hydroxy-3-phenyl-propylamine of formula I is obtained, after elimination of the solvent, with a high chemical purity (generally >96%) and optical purity (generally >94% ee).

In a preferred embodiment of the process the product of the catalytic hydrogenation is then converted into a salt. The purpose of this is to make it easier to isolate the 3-hydroxy-3-phenyl-propylamines and further increase the enantiomeric purity, preferably to levels >99%. In addition, this produces solids which can be transported and stored. Thus, for example, salts with inorganic acids such as hydrochloric acid, sulphuric acid, hydrobromic acid, phosphoric acid, sulphonic acid or organic acids, such as oxalic acid, maleic acid, fumaric acid, citric acid, succinic acid or acetic acid, can be formed. It is also possible to use mixtures of the above-mentioned acids. To increase the enantiomeric purity, however, chiral salt-forming agents such as chiral mandelic acid, lactic acid or tartaric acid may be used, although this is not essential.

The above process is particularly preferably used to prepare the compound of formula I-A,

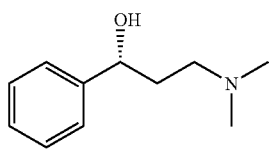

I-A which is reacted in later reaction steps to form R-atomoxetine. This process is also particularly preferable for preparing the compound of formula I-B,

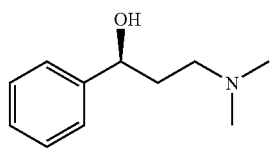

I-B which is also reacted in later reaction steps to form R-atomoxetine or S-fluoxetine. The above process is also particularly preferred for preparing a compound of formula I-C,

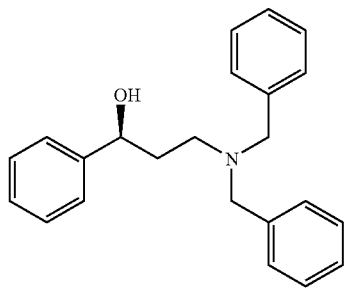

I-C which is reacted in later reaction steps to form S-norfluoxetine.

TERMS AND DEFINITIONS USED

The term "$C_{1-6}$-alkyl" (including those which are part of other groups) denotes branched and unbranched alkyl groups with 1 to 6 carbon atoms, while the term "$C_{1-4}$ alkyl" accordingly denotes branched and unbranched alkyl groups with 1 to 4 carbon atoms. Preferred are alkyl groups with 1 to 4 carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. are optionally also used for the above-mentioned groups. Unless otherwise stated, the definitions propyl, butyl, pentyl and hexyl include all possible isomeric forms of the groups in question. Thus, for example, propyl includes n-propyl and iso-propyl, butyl includes iso-butyl, sec-butyl and tert-butyl etc.

By the term "$C_{1-8}$-alcohol" are meant branched and unbranched alcohols with 1 to 8 carbon atoms and one or two hydroxy groups. Accordingly, the term "$C_{1-4}$-alcohol" denotes branched and unbranched alkyl groups with 1 to 4 carbon atoms and one or two hydroxy groups. Alcohols with 1 to 4 carbon atoms are preferred. The following are mentioned by way of example: methanol, ethanol, n-propanol, iso-propanol, n-butanol, iso-butanol, sec-butanol, tert-butanol, n-pentanol, iso-pentanol, neo-pentanol or hexanol. The abbreviations MeOH, EtOH, n-PrOH, i-PrOH, n-BuOH, i-BuOH, t-BuOH, etc. may optionally also be used for the above-mentioned molecules. Unless otherwise stated, the definitions propanol, butanol, pentanol and hexanol include all possible isomeric forms of the groups in question. Thus, for example, propanol includes n-propanol and iso-propanol, butanol includes iso-butanol, sec-butanol and tert-butanol etc.

The term "aryl" (including those which are part of other groups) denotes aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

The term "$C_{7-18}$-aralkyl" (including those which are part of other groups) denotes branched and unbranched alkyl groups with 1 to 8 carbon atoms which are substituted by an aromatic ring system with 6 or 10 carbon atoms, and accordingly the term "$C_{7-11}$-aralkyl" includes branched and unbranched alkyl groups with 1 to 4 carbon atoms which are substituted by an aromatic ring system with 6 carbon atoms. Examples include: benzyl, 1- or 2-phenylethyl. Unless otherwise stated, the aromatic groups may be substituted by one or more groups selected from among methyl, ethyl, iso-propyl, tert-butyl, hydroxy, fluorine, chlorine, bromine and iodine.

The compounds of formula I and II may optionally be converted into the acid addition salts thereof with an inorganic or organic acid. Suitable acids include for example succinic acid, hydrobromic acid, acetic acid, fumaric acid, maleic acid, methanesulphonic acid, lactic acid, oxalic acid, phosphoric acid, hydrochloric acid, sulphuric acid, tartaric acid or citric acid. Mixtures of these acids may also be used.

The process according to the invention will now be illustrated by the Examples that follow. The skilled man will be aware that the Examples are intended only as an illustration and are not to be regarded as limiting.

EXAMPLES

I) Synthesis of the Ketone Precursors
1) 3-N,N-dimethylamino-1-phenyl-propan-1-one hydrochloride: 480.6 g (4.0 mol) acetophenone are dissolved in 1.0 L iso-propanol and 132.1 g (4.4 mol) paraformaldehyde are added with stirring, then 326.2 g (4.0 mol) dimethylamine-hydrochloride are added and the mixture is rinsed with another 100 ml of iso-propanol. It is heated to 90° C. for five hours, then cooled to about 4° C. and the solid formed is suction filtered and washed with 200 mL cold iso-propanol and then with 600 mL acetone. The 557.6 g crude product are then dried at 50° C. in vacuo, yield 512.4 g (59,9%), purity >98% according to NMR.
2) 3-(benzyl-methyl-amino)-1-phenyl-propan-1-one hydrochloride: 114.0 g (0.95 mol) acetophenone are dissolved in 73 mL ethanol and with stirring 28.5 g 0.95 mol) paraformaldehyde are added, then 149.8 g (0.95 mol) N-benzyl, N-methylamine-hydrochloride are added and the mixture is rinsed with another 30 ml of ethanol. The mixture is heated to 82° C. for five hours, then cooled to about 20° C., diluted with 50 mL ethanol and the solid formed is suction filtered and washed with 150 mL ethanol. The 237 g crude product are then dried at 50° C. in vacuo, yield 212.8 g (77.3%), purity >97% according to HPLC.

II) Hydrogenations 1) (S)-3-N,N-dimethylamino-1-phenyl-propan-1-ol: 373 g (1.745 mol) 3-N,N-dimethylamino-1-phenyl-propan-1-one hydrochloride are suspended in 1.65 litres methanol and 0.19 litres water under nitrogen, 88 mg bis-(1,5-cyclooctadiene)-dirhodium(I)-dichloride, 187 mg RR-MCCPM ligand and 746 mg sodium hydrogen carbonate are added and the suspension is hydrogenated at 30° C. and 100 bar hydrogen pressure for about 10 hours. The reaction mixture is evaporated down and the residue obtained is distributed between 1.0 L water and 0.4 L organic solvent (toluene or dichloromethane). The pH is adjusted to 1.5 with 32% hydrochloric acid and the mixture is stirred for 10 minutes, then the aqueous phase is separated off. The organic phase is again combined with 0.3 L water, stirred and the aqueous phase is separated off again. The combined aqueous phases are now adjusted to a pH of 9.0 with 1.0 L organic solvent and 45% sodium hydroxide solution, stirred, and then the phases are separated. The aqueous phase is again extracted with 0.5 L solvent and the combined organic phases are evaporated down at 60° C. and 7 mbar. The yield is 271.7 g (86.9%), purity >98% (NMR), enantiomeric purity 94.5% (HPLC).

2) (S)-3-N-benzyl,N-methylamino-1-phenyl-propan-1-ol: 15 g (52 mmol) 3-(benzyl-methyl-amino)-1-phenyl-propan-1-one hydrochloride are suspended in 135 mL methanol and 15 mL water under nitrogen, 5.7 mg of bis-(1,5-cyclooctadiene)-dirhodium(I)-dichloride, 12.1 mg RR-MCCPM ligand and 30 mg sodium hydrogen carbonate are added and the suspension is hydrogenated at 30° C. and 100 bar hydrogen pressure for about 24 hours. The reaction mixture is evaporated down and the residue obtained is distributed between 70 mL water and 70 mL organic solvent (toluene or dichloromethane). The pH is adjusted to 1.4 with 32% hydrochloric acid and the mixture is stirred for 10 minutes, then the aqueous phase is separated off. The organic phase is again combined with 40 mL water, stirred and the aqueous phase is separated off again. The combined aqueous phases are then extracted again with 10 mL organic solvent, then combined with 60 mL solvent and adjusted to a pH of 6.4 with 45% sodium hydroxide solution, stirred, and then the phases are separated. The aqueous phase is again extracted with 30 mL solvent and the combined organic phases are evaporated down at 60° C. and 5 mbar. The yield is 10.72 g (80.8%), purity >98% (NMR), enantiomeric purity 94% (NMR).

III) Salts of the Hydrogenated Aminoalcohols 1) (S)-3-N,N-dimethylamino-1-phenyl-propan-1-ol-oxalate: 17.9 g (S)-3-N,N-dimethylamino-1-phenyl-propan-1-ol, enantiomeric purity 94% (NMR) is dissolved in 188 ml iso-propanol and then 9.0 g oxalic acid is added with stirring. The mixture is combined with another 107 ml iso-propanol and refluxed for 15 minutes, then cooled to about 40° C. The thick suspension obtained is combined with another 36 ml of iso-propanol and cooled to about 20° C., then filtered and washed with 100 ml iso-propanol. The crude product is dried at 50° C. in vacuo and 24.0 g (89% of theor.) of (S)-3-N,N-dimethylamino-1-phenyl-propan-1-ol-oxalate are obtained in the form of white crystals, enantiomeric purity 96.3% (HPLC), melting point 125-126° C.

2a) (S)-3-N-benzyl,N-methylamino-1-phenyl-propan-1-ol-mandelate: 2.55 g (S)-3-N-benzyl,N-methylamino-1-phenyl-propan-1-ol, enantiomeric purity 94% (NMR) is dissolved in 8.1 ml of toluene and 1.52 g D-(−)-mandelic acid is added with stirring. The mixture is diluted with 8.1 ml of toluene, cooled to about 3° C. and the crystals are suction filtered and washed with 12 ml cold toluene. After drying at 50° C. in vacuo 3.37 g (83%) of the (S)-3-N-benzyl,N-methylamino-1-phenyl-propan-1-ol-mandelate are obtained, enantiomeric purity 100% (HPLC), melting point 142-143° C.

2b) (S)-3-N-benzyl,N-methylamino-1-phenyl-propan-1-ol-hydrochloride: 2.55 g (S)-3-N-benzyl,N-methylamino-1-phenyl-propan-1-ol, enantiomeric purity 94% (NMR) is dissolved in 5.8 ml of toluene and 1.83 g 20% isopropanolic hydrochloric acid are added with stirring. The mixture is cooled to about 3° C., the crystals are suction filtered and washed with 9.5 ml cold toluene. After drying at 60° C. in vacuo, 1.69 g (58%) of the (S)-3-N-benzyl,N-methylamino-1-phenyl-propan-1-ol-hydrochloride are obtained, enantiomeric purity 95.4% (HPLC).

What is claimed is:

1. A process for preparing chiral 3-hydroxy-3-phenyl-propylamine of formula I,

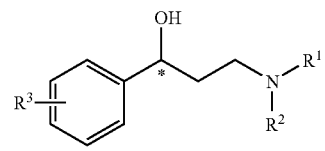

wherein
$R^1$ denotes H, —$C_{1-6}$-alkyl or —$C_{7-18}$-aralkyl;
$R^2$ denotes H, —$C_{1-6}$-alkyl or —$C_{7-18}$-aralkyl;
$R^3$ denotes H, —$C_{1-6}$-alkyl, —OH, —O—$C_{1-6}$-alkyl, —O—$C_{7-18}$-aralkyl, —OOC—$C_{1-6}$-alkyl, —OOC-aryl or halogen;
or an acid addition salt thereof, starting from 1-amino-3-(phenyl)-propan-3-one of formula II,

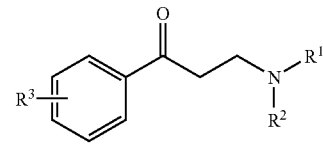

wherein $R^1$, $R^2$, and $R^3$ are as hereinbefore defined, or an acid addition salt thereof, characterised in that the latter is subjected to asymmetrical hydrogenation in the presence of a catalyst system consisting of rhodium and chiral 4-(dicyclohexyl-phosphino)-2-(diphenylphosphino-methyl)-N-methyl-aminocarbonyl-pyrrolidine, optionally an inert diluent containing water and a weak base.

2. The process according to claim 1 wherein
$R^1$ denotes H, methyl, ethyl, iso-propyl, tert-butyl or benzyl;
$R^2$ denotes H, methyl, ethyl, iso-propyl, tert-butyl or benzyl;
$R^3$ denotes H, methyl, iso-propyl, tert-butyl, hydroxy, methoxy, propoxy, butoxy, benzyloxy, acetyloxy, benzoyloxy, F, Cl or Br.

3. The process for preparing S-3-hydroxy-3-phenyl-propylamines I-S according to claim 1,

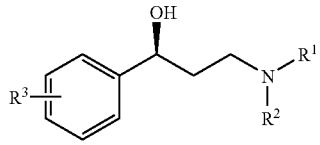

wherein the catalyst system consists of rhodium and (2R, 4R)-4-(dicyclo-hexylphosphino)-2-(diphenylphosphino-methyl)-N-methyl-aminocarbonyl-pyrrolidine.

4. The process for preparing R-3-hydroxy-3-phenyl-propylamines I-R according to claim 1,

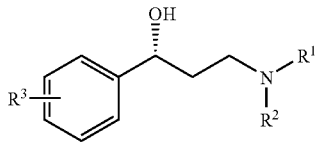

wherein the catalyst system consists of rhodium and (2S, 4S)-4-(dicyclo-hexylphosphino)-2-(diphenylphosphino-methyl)-N-methyl-aminocarbonyl-pyrrolidine.

5. The process according to claim 1, wherein the hydrogenation is carried out in the presence of less than one equivalent of a weak base selected from among the tertiary amines, alkali metal hydrogen carbonates, alkali metal-carbonates and the free base 1-(N-alkyl-N-methylamino)-3-(2-thienyl)-propan-3-one.

6. The process according to claim 1, characterised in that the asymmetric hydrogenation is carried out in a temperature range of from 0° C. to 100° C.

7. The process according to claim 1, characterised in that the asymmetric hydrogenation is carried out under a pressure of from 1 to 150 bar.

8. The process according to claim 1, characterised in that the asymmetric hydrogenation is carried out in a protic diluent.

9. The process according to claim 8, characterised in that the diluent for the asymmetric hydrogenation comprises water.

10. The process according to claim 1, wherein a compound of formula II or an acid addition salt thereof is used in a molar ratio of 500:1 to 100000:1 to the rhodium catalyst in the asymmetrical hydrogenation.

11. The process according to claim 1, wherein the rhodium catalyst is used as a pre-prepared solution for the asymmetric hydrogenation.

12. The process according to claim 1, wherein the rhodium catalyst for the asymmetric hydrogenation is prepared in situ.

13. The process according to claim 1, wherein the asymmetric hydrogenation is carried out within a reaction period of from 2 to 48 hours.

14. The process according to claim 1, further comprising the steps of:
(i) dividing the reaction mixture obtained in the asymmetrical hydrogenation between water and an organic solvent,
(ii) adjusting the pH value of the aqueous phase in the acid range,
(iii) separating off the aqueous phase,
(iv) adjusting the pH value of the aqueous phase in the basic range;
(v) dividing the reaction mixture between water and an organic solvent,
(vi) separating off the organic phase formed, and
(vii) concentrating the so-separated organic phase.

15. The process according to claim 1, wherein the product of the catalytic hydrogenation is converted into a salt.

16. A process for preparing chiral 3-hydroxy-3-phenyl-propylamine of formula I,

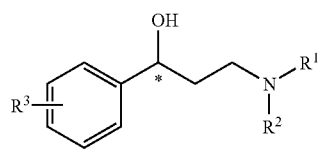

wherein
R$^1$ denotes H, —C$_{1-6}$-alkyl or —C$_{7-18}$-aralkyl;
R$^2$ denotes H, —C$_{1-6}$-alkyl or —C$_{7-18}$-aralkyl;
R$^3$ denotes H, —C$_{1-6}$-alkyl, —OH, —O—C$_{1-6}$-alkyl, —O—C$_{7-18}$-aralkyl, —OOC—C$_{1-6}$-alkyl, —OOC-aryl or halogen;
or an acid addition salt thereof, starting from 1-amino-3-(phenyl)-propan-3-one of formula II,

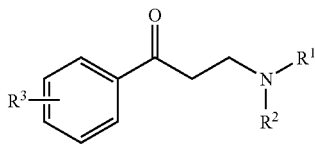

wherein R$^1$, R$^2$, and R$^3$ are as hereinbefore defined, or an acid addition salt thereof, characterised in that the latter is subjected to asymmetrical hydrogenation in the presence of a catalyst system consisting of rhodium and chiral 4-(dicyclohexyl-phosphino)-2-(diphenylphosphino-methyl)-N-methyl-aminocarbonyl-pyrrolidine, and a protic diluent comprising water.

17. A process for preparing chiral 3-hydroxy-3-phenyl-propylamine of formula I,

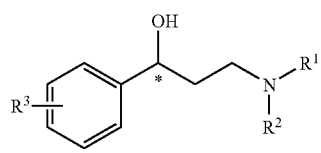

wherein
R$^1$ denotes H, —C$_{1-6}$-alkyl or —C$_{7-18}$-aralkyl;
R$^2$ denotes H, —C$_{1-6}$-alkyl or —C$_{7-18}$-aralkyl;
R$^3$ denotes H, —C$_{1-6}$-alkyl, —OH, —O—C$_{1-6}$-alkyl, —O—C$_{7-18}$-aralkyl, —OOC—C$_{1-6}$-alkyl, —OOC-aryl or halogen;
or an acid addition salt thereof, starting from 1-amino-3-(phenyl)-propan-3-one of formula II,

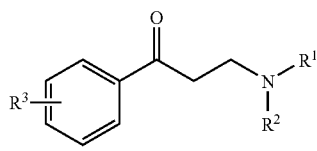

wherein $R^1$, $R^2$, and $R^3$ are as hereinbefore defined, or an acid addition salt thereof, characterised in that the latter is subjected to asymmetrical hydrogenation in the presence of a catalyst system consisting of rhodium and chiral 4-(dicyclohexyl-phosphino)-2-(diphenylphosphino-methyl)-N-methyl-aminocarbonyl-pyrrolidine, optionally an inert diluent and a weak base, further comprising the steps of:

(i) dividing the reaction mixture obtained in the asymmetrical hydrogenation between water and an organic solvent,
(ii) adjusting the pH value of the aqueous phase in the acid range,
(iii) separating off the aqueous phase,
(iv) adjusting the pH value of the aqueous phase in the basic range;
(v) dividing the reaction mixture between water and an organic solvent,
(vi) separating off the organic phase formed, and
(vii) concentrating the so-separated organic phase.

* * * * *